(12) United States Patent
Kniewasser

(10) Patent No.: US 9,016,277 B2
(45) Date of Patent: Apr. 28, 2015

(54) COMPRESSED AIR CONTROL DEVICE FOR A CPAP DEVICE AND CORRESPONDING CPAP SYSTEM

(75) Inventor: Gert Kniewasser, Greifenberg (DE)

(73) Assignee: Medin Medical Innovations GmbH, Puchheim (DE)

( * ) Notice: Subject to any disclaimer, the term of this patent is extended or adjusted under 35 U.S.C. 154(b) by 475 days.

(21) Appl. No.: 13/508,523

(22) PCT Filed: Aug. 27, 2010

(86) PCT No.: PCT/EP2010/062572
§ 371 (c)(1),
(2), (4) Date: Jul. 30, 2012

(87) PCT Pub. No.: WO2011/054556
PCT Pub. Date: May 12, 2011

(65) Prior Publication Data
US 2012/0304996 A1    Dec. 6, 2012

(30) Foreign Application Priority Data
Nov. 9, 2009 (DE) .................. 10 2009 046 541

(51) Int. Cl.
*A61M 11/00* (2006.01)
*A61M 16/12* (2006.01)
*A61M 16/00* (2006.01)

(52) U.S. Cl.
CPC ....... *A61M 16/12* (2013.01); *A61M 2016/0021* (2013.01); *A61M 2016/0027* (2013.01); *A61M 2016/0039* (2013.01); *A61M 16/127* (2014.02); *A61M 2240/00* (2013.01)

(58) Field of Classification Search
USPC ............................ 128/204.18, 204.21, 204.23
See application file for complete search history.

(56) References Cited

U.S. PATENT DOCUMENTS

| 4,401,115 | A | 8/1983 | Monnier |  |
|---|---|---|---|---|
| 4,644,947 | A * | 2/1987 | Whitwam et al. | 128/204.25 |
| 7,866,318 | B2 * | 1/2011 | Bassin | 128/204.23 |
| 2004/0020488 | A1 | 2/2004 | Kniewasser |  |
| 2009/0126731 | A1 | 5/2009 | Dunsmore et al. |  |
| 2009/0326403 | A1 * | 12/2009 | Bassin et al. | 600/538 |

FOREIGN PATENT DOCUMENTS

| EP | 1161963 A1 | 12/2001 |
|---|---|---|
| WO | 99/24101 A1 | 5/1999 |

OTHER PUBLICATIONS

International Search Report corresponding to PCT Application No. PCT/EP2010/062572, mailed Nov. 30, 2010 (German and English language document) (6 pages).

* cited by examiner

*Primary Examiner* — Steven Douglas
(74) *Attorney, Agent, or Firm* — Maginot, Moore & Beck, LLP

(57) ABSTRACT

A compressed air control device for a CPAP device comprises a pressure measuring device for measuring a variation of the pressure in a hollow body of the CPAP device and for generating a corresponding pressure signal, a pressure variation evaluating device for evaluating the measured variation of the pressure according to at least one predetermined criterion and for generating a pressure modulation control signal based on the result of the evaluation, and a pressure modulating device for receiving a substantially constant compressed air stream and for outputting a modulated compressed air stream to the CPAP device. The pressure modulating device is configured in such a way that, in response to the pressure modulation control signal, it modulates the pressure of the compressed air stream output to the CPAP device.

11 Claims, 3 Drawing Sheets

COMPRESSED AIR CONTROL DEVICE FOR A CPAP DEVICE AND CORRESPONDING CPAP SYSTEM

This application is a 35 U.S.C. §371 National Stage Application of PCT/EP2010/062572, filed on Aug. 27, 2010, which claims the benefit of priority to Application Serial No. 10 2009 046 541.3, filed on Nov. 9, 2009 in Germany, the disclosures of which are incorporated herein by reference in their entirety.

BACKGROUND

The present invention relates to a compressed air control device for a CPAP device and a corresponding CPAP system.

The principle of a device for producing a continuous positive airway pressure, abbreviated to CPAP device, and in particular a nasal CPAP device, abbreviated to nCPAP device, is that a patient treated therewith breathes in and out with pressure support.

An extremely important application is in the treatment of premature babies. In this case, the effect is that the lung, which is not yet fully developed, is inflated by the overpressure and improved gas exchange is possible as a result. Another very important factor is that the dangerous collapse of the alveoli owing to the negative respiratory pressure can be prevented by this technology. Another aspect is that the alveoli are opened better, and thus the entire functional state of the lung is improved.

FIG. 3 is a schematic view of the device 1, known from WO 99/24101, for producing a continuous positive airway pressure.

Reference numeral 10 denotes a cylindrical hollow body 10 in which an overpressure can be built up and reference numeral 20 denotes a first opening, provided in the outer surface of the cylindrical hollow body 10, for supplying a constant compressed air stream A, which is directed into the hollow body 10, and for removing the exhaled air stream B. A connecting piece 30, which can be attached to an end face 10a of the cylindrical hollow body 10 for connecting the hollow body 10 to a nose attachment 100, and a spacer 40, which can be attached to the hollow body 10 and to which a flow nozzle 50 for directing the constant compressed air stream A towards the first opening 20 can be attached, are also provided. The flow nozzle comprises a connecting pipe L4b for attaching a compressed air line for supplying the constant compressed air stream A.

The connecting piece 30 consists of a Teflon plug which can be inserted, at least in part, into the hollow body 10 at the end face 10a. The plug comprises two passages (dashed lines) which correspond to corresponding airways of the nose attachment 100. Two outward-facing pipe ends 35 for insertion into the nose attachment 100 are provided in the passages of the connecting piece 30.

A second opening O2 for connecting a pressure gauge is provided at the other end face 10b of the cylindrical hollow body 10. For this purpose, a pipe 60 for connection to a pressure sensing line is connected to the second opening at substantially a right angle. The pipe 60 extends away from the hollow body 10 by substantially the same length as the flow nozzle 50, and therefore a line for supplying compressed air to the flow nozzle can be attached to the flow nozzle 50 at substantially the same height as the pressure sensing line.

The spacer 40 has a substantially annular shape. The flow nozzle 50 is guided through a hole in the side wall of the annular shape and directed towards the first opening 20 in a substantially perpendicular manner. The flow nozzle 50 projects into the interior of the annular shape by a predetermined length.

The side wall of the annular shape comprises a safety air passage opening 45. The annular shape of this construction can be sealed by the fingers in such a way that the exhaled air stream B flows through the safety air passage opening 45.

The idea underlying this known device for producing a continuous positive airway pressure is that a Benveniste valve is provided, the cavity of which can be made accessible from one side over a large cross-section by removing the connecting piece, in such a way that effective sterilisation of the cavity is possible. An exhalation tube is not required during operation.

A drawback of the known CPAP and nCPAP devices is the fact that they are not flexible when handling compressed air and during operation using compressed air production means and pressure gauges.

SUMMARY

The compressed air control device for a CPAP device and the corresponding CPAP system according to the present disclosure have the advantage that the state of the patient, which is reflected in the analysed pressure signal of the CPAP device, can be responded to in a more flexible manner during CPAP treatment.

It is thus possible, for example, to output pressure pulses which are correlated or synchronised with natural breathing reflexes.

In addition, breathing activity which is subject to life-threatening apnoeic phases, for example, can be recognised, and this can be responded to by a pressure pulse to stimulate natural breathing.

It is particularly advantageous that the breathing activity can be detected directly via the hollow body of the CPAP device, which functions according to the Benveniste principle.

Advantageous developments of and improvements to the respective subject-matters of the invention are found in the dependent claims.

According to a preferred development, the pressure curve evaluation means is formed to produce a flow control signal on the basis of the result of the evaluation, a flow control device being provided which is formed in such a way that it controls a flow of the substantially constant compressed air stream in response to the flow control signal. For example, a basic flow which is modulated in accordance with the flow control signal could be provided in an analogous manner to the pressure.

According to another preferred development, the pressure curve evaluation means comprises a storage means in which reference pressure curves are stored, and the pressure curve evaluation means is formed in such a way that it carries out a comparison with the reference pressure curves during the evaluation.

According to another preferred development, the flow control device is fed by an air supply means and by an oxygen supply means and is formed in such a way that it can adjust a concentration ratio of air and oxygen.

According to another preferred development, the compressed air evaluation means is formed in such a way that it detects an apnoeic phase during the evaluation and, in response to a detection of this type, outputs to the pressure modulation device a pressure modulation control signal to trigger a pressure pulse in the modulated compressed air stream.

According to another preferred development, the pressure curve evaluation means for recognising an apnoeic phase detects whether the detected pressure in the hollow body is substantially constant for a predetermined period, the predetermined period preferably being in the range from 2 to 5 s.

According to another preferred development, the pressure curve evaluation means is formed in such a way that it detects natural breathing reflexes during the evaluation and, in response to a detection of this type, outputs to the pressure modulation device a pressure modulation control signal to trigger a pressure pulse in the modulated compressed air stream, which pulse is correlated with the natural breathing reflex.

According to another preferred development, the pressure curve evaluation means for recognising the start of natural breathing reflexes detects whether the pressure has a predetermined trailing edge.

According to another preferred development, the pressure modulation device is formed in such a way that it can provide a predefinable basic modulation in the modulated compressed air stream, in particular a periodic modulation.

According to another preferred development, each pressure pulse is substantially rectangular.

BRIEF DESCRIPTION OF THE DRAWINGS

Embodiments of the invention are shown in the drawings and described in more detail in the following description.

In the drawings.

DETAILED DESCRIPTION

Figure 1:
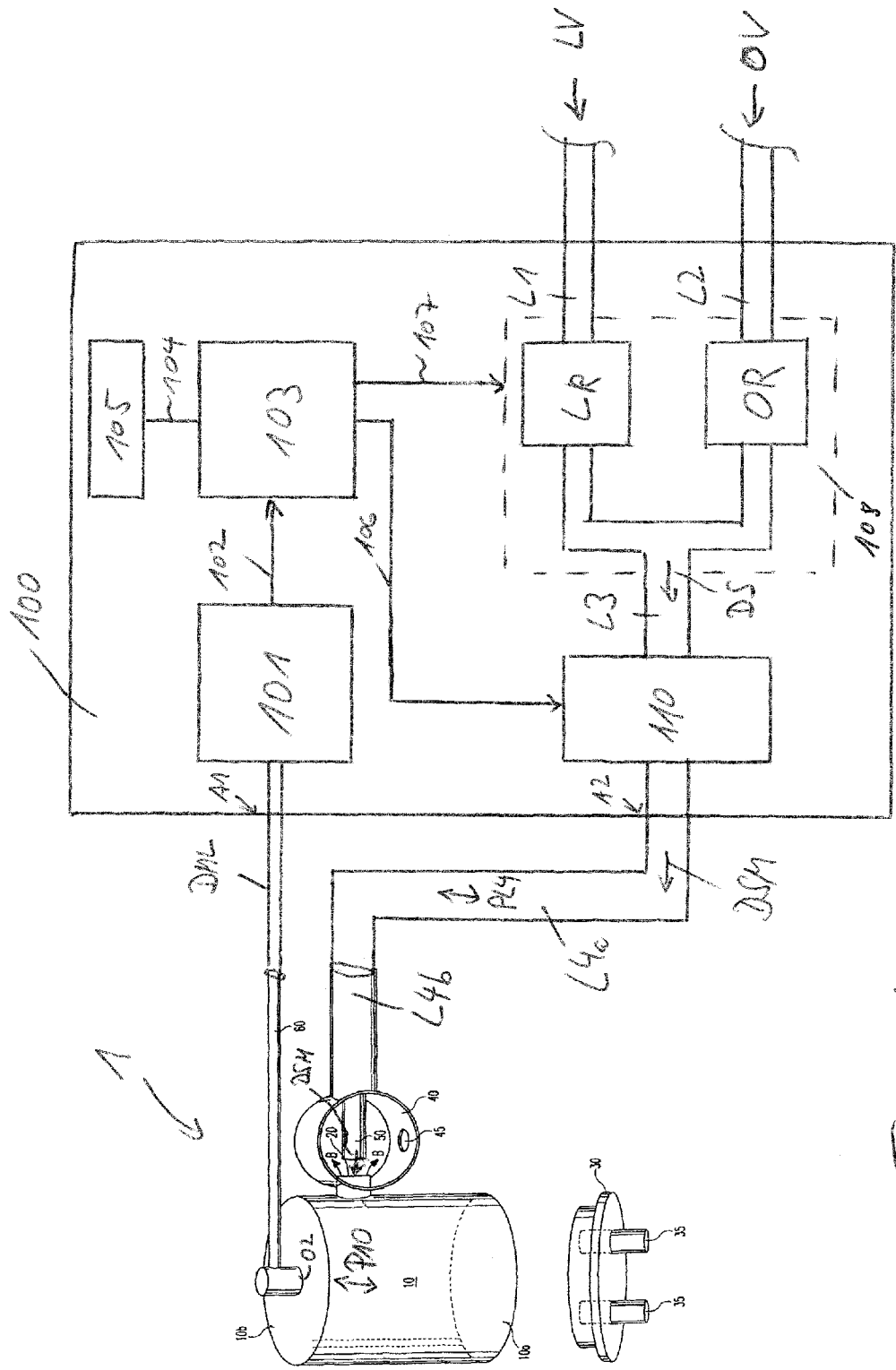
FIG. 1 is a schematic view of an embodiment of the CPAP system according to the invention comprising a corresponding embodiment of the compressed air control device according to the invention.

In all the figures, like reference numerals denote like or functionally like components.

FIG. 1 is a schematic view of an embodiment of the CPAP system according to the invention comprising a corresponding embodiment of the compressed air control device according to the invention.

In FIG. 1, reference numeral 1 denotes a CPAP device which corresponds to the CPAP device which is known per se and has already been described in connection with FIG. 3.

Reference numeral P10 has additionally been introduced in the hollow body 10 and denotes a pressure in the hollow body, which pressure varies over time and can be detected via the second opening O2 and the pipe 60.

Figure 3:
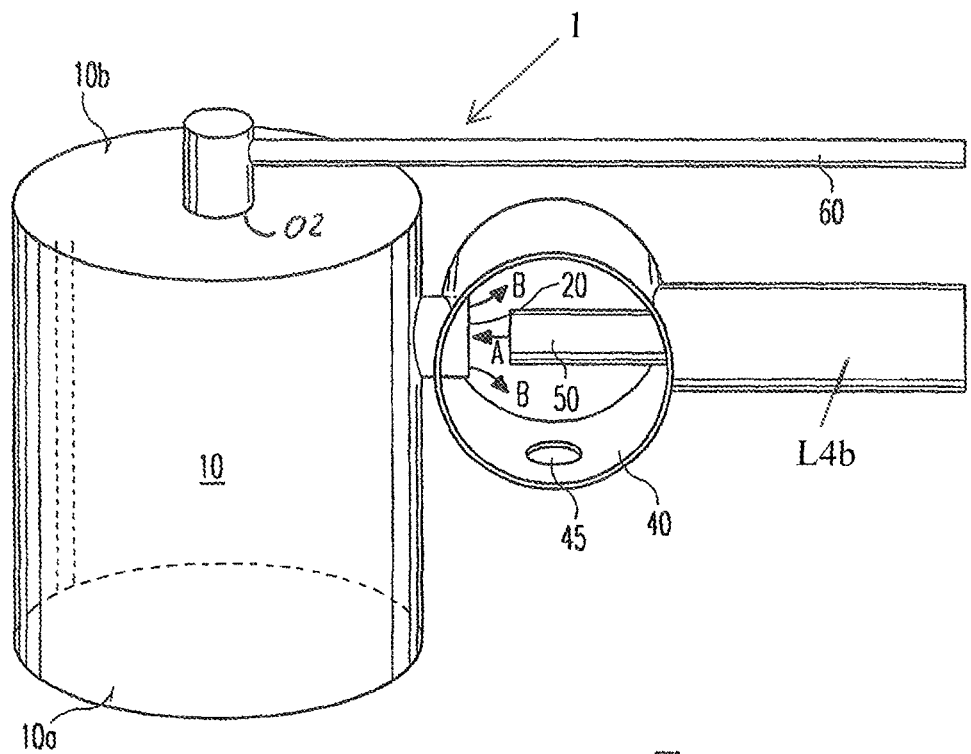
FIG. 3 is a schematic view of the device, known from WO 99/24101, for producing a continuous positive airway pressure.
Figure 3:
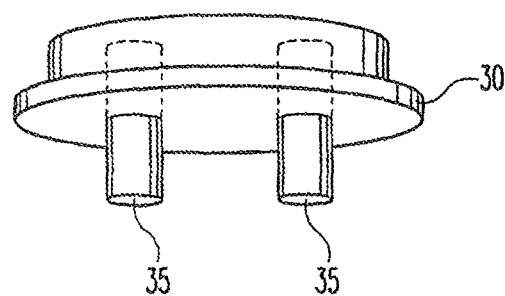

In addition, in this embodiment according to the invention, the hollow body 10 is no longer supplied with a constant compressed air stream A via the first opening 20, as in the prior art of FIG. 3, but rather with a modulated compressed air stream DSM which is produced by a compressed air control device 100 in response to the detected pressure P10 in the hollow body.

The compressed air control device 100 comprises a first outlet A1 for connecting a pressure sensing line DML which is connected to the pipe 60 of the CPAP device 1.

A pressure detection means 101, for example a pressure sensor, receives the pressure P10 in the hollow body 10 of the CPAP device 1 via the pressure sensing line DML. It should be noted that the detected pressure P10 directly reflects the breathing activity of the patient, since the patient inhales from and exhales into the hollow body 10.

The pressure sensor 101 produces from the detected pressure P10 a corresponding electrical pressure signal 102 which is output to a pressure curve evaluation means 103, 104, 105 which comprises a storage means 105 connected thereto via a line 104.

The pressure curve evaluation means 103, 104, 105 evaluates the pressure curve, detected by the pressure sensor 101, of the pressure P10 in accordance with at least one predetermined criterion and produces a pressure modulation control signal 106 on the basis of the result of the evaluation.

In this embodiment, predetermined criteria, for example reference pressure curves, are stored in the storage means 105 and can be drawn on for comparison during the evaluation.

The detected pressure curve and optionally also the result of the evaluation can be represented visually on a display means (not shown). Acoustic and/or optical warning means for dangerous situations which can be derived from the detected pressure curve may also be provided.

Reference numeral 110 denotes a pressure modulation device which receives a substantially constant compressed air stream DS and outputs a modulated compressed air steam DSM to the CPAP device 1, specifically via the second outlet A2, which is connected to the connecting pipe L4b of the CPAP device via a pressure supply line L4a.

The pressure curve evaluation means 103, 104, 105 also produces a flow control signal 107 which is transmitted to a flow control device 108 connected upstream of the pressure modulation device 110.

The flow control device 108 is fed by an air supply means LV (not shown) and by an oxygen supply means OV (not shown) and is formed in such a way that it can also adjust, in addition to the flow of the resulting constant compressed air stream DS which is supplied to the pressure modulation device 110, a concentration ratio of air and oxygen.

The flow control device 108 comprises an internal air regulation means LR and an oxygen regulation means OR connected in parallel therewith, which are fed by the corresponding supply means LV, OV via respective lines L1 and L2.

The output line of the flow control device 108 to the pressure modulation device 110 is denoted by reference numeral L3.

Using a compressed air control device constructed in this manner for a CPAP device, it is possible to supply the CPAP device with a modulated compressed air stream DSM which has any desired pressure patterns, which can be triggered via the detected pressure signal in the hollow body 10 of the CPAP device 1.

Since the patient inhales from and exhales into the hollow body, information about the patient's breathing can be extracted from the detected curve of the pressure P10.

By analysing, in the pressure curve evaluation means 103, 104, 105, the electrical signal 102 corresponding to the pressure curve, it is possible to respond to specific situations in the breathing via particular pressure patterns, as will be described in more detail below with reference to FIG. 2.

Figure 2:
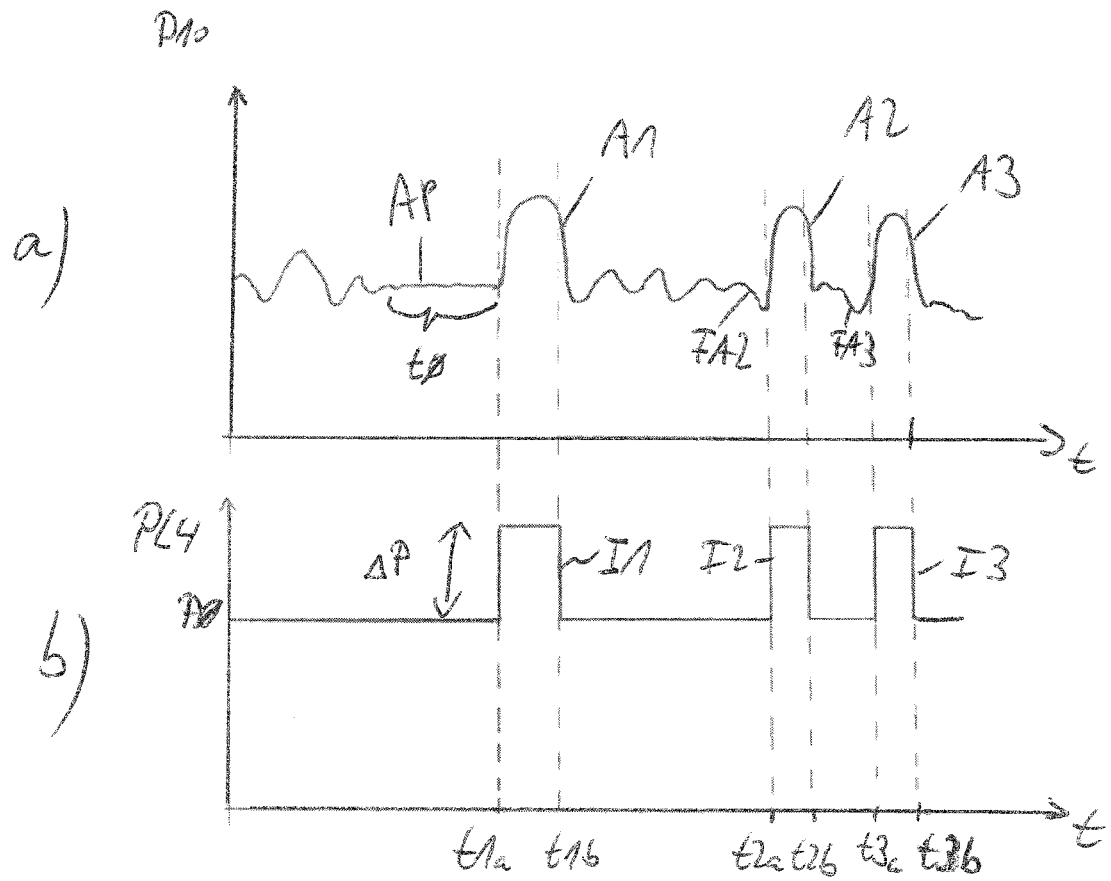
FIG. 2a,b show the detected pressure in the hollow body and the corresponding modulated pressure in the pressure supply line over time.

FIG. 2 shows the detected pressure in the hollow body and the corresponding modulated pressure in the pressure supply line over time.

In FIG. 2, t denotes the time axis, FIG. 2a) showing the trend with respect to time of the pressure P10 in the hollow body 10 of the CPAP device 1 and FIG. 2b) showing the pressure PL4 of the pressure supply line L4a of the CPAP device 1.

With reference to FIG. 2a), an apnoeic phase AP is initially detected by the pressure curve evaluation means, which phase is expressed in that the pressure P10 is virtually constant for a predetermined period t0 of typically 2-5 s. After detection of an apnoeic phase AP of this type, the pressure curve evaluation means 103, 104, 105 outputs a pressure modulation control signal 106 to the pressure modulation device 110, which, starting from an overpressure P0, initialises a pressure pulse I1 which is rectangular and has an amplitude ΔP. The duration of the pressure pulse I1 is from time t1a to time t1b and causes a corresponding pressure pulse A1 in the hollow body 10 of the CPAP device 1. This pressure pulse I1 and the resulting pressure pulse A1 are intended to stimulate the spontaneous breathing of the patient.

Over the further course of time, the pressure curve evaluation means 103, 104, 105 detects a trailing edge FA2 of the pressure P10, which edge is indicative that a spontaneous breathing reflex of the patient starts at its end.

Therefore, the pressure curve evaluation means 103, 104, 105 causes, via a corresponding pressure modulation control signal 106, the pressure modulation device 110 to output a pressure pulse I2, which extends from time t2a to time t2b and also has an amplitude ΔP starting from the basic overpressure P0.

With reference to FIG. 2a), the pressure pulse I2 thus supports the natural breathing of the patient, which breathing is expressed in the pressure pulse A2 of the pressure P10.

According to FIG. 2a), a further spontaneous breathing reflex is then detected by means of the trailing edge FA3, which reflex is supported in the time period from t3a to t3b by a corresponding pressure pulse I3 of the pressure modulation device 110.

Although the present invention has been described above with reference to a preferred embodiment, it is not limited thereto but can be modified in a variety of ways.

Although in the above embodiment a breathing simulation in response to an apnoeic phase and breathing support correlated to natural breathing reflexes have been described, it is obviously possible for any other pressure patterns to be output from the pressure modulation device 110 to the CPAP device. It is obviously also possible for other criteria besides the detected pressure P10 in the hollow body 10 to be used, for example patient parameters input into the pressure control device 100.

In addition to a result-based modulation, a basic modulation, for example a periodic pressure pattern such as an oscillating sinusoidal pressure pattern can also be provided in the pressure supply line L4a.

The invention claimed is:

1. Compressed air control device for a CPAP device comprising:
   a pressure detection device for detecting a pressure curve of the pressure in a hollow body of the CPAP device and for producing a corresponding pressure signal;
   a pressure curve evaluation means for evaluating the detected pressure curve of the pressure in accordance with at least one predetermined criterion and for producing a pressure modulation control signal on the basis of the result of the evaluation; and
   a pressure modulation device for receiving a substantially constant compressed air stream and for outputting a modulated compressed air stream to the CPAP device, which pressure modulation device is formed in such a way that it modulates a pressure of the compressed air stream output to the CPAP device in response to the pressure modulation control signal;
   wherein the pressure curve evaluation means is formed in such a way that it detects an apnoeic phase during the evaluation and, in response to a detection of this type, outputs to the pressure modulation device a pressure modulation control signal to trigger a pressure pulse in the modulated compressed air stream; wherein the pressure curve evaluation means for recognising an apnoeic phase detects whether the pressure is substantially constant for a predetermined period, the predetermined period preferably being in the range from 2 to 5 s;
   wherein the pressure curve evaluation means is formed in such a way that it detects natural breathing reflexes during the evaluation and, in response to a detection of this type, outputs to the pressure modulation device a pressure modulation control signal to trigger a pressure pulse in the modulated compressed air stream, which pulse is correlated with the natural breathing reflex; and
   wherein the pressure pulses are synchronised with natural breathing reflexes.

2. Compressed air control device according to claim 1, wherein the pressure curve evaluation means is formed to produce a flow control signal on the basis of the result of the evaluation and a flow control device is provided which is formed in such a way that it controls a flow of the substantially constant compressed air stream in response to the flow control signal.

3. Compressed air control device according to claim 1, wherein the pressure curve evaluation means comprises a storage means in which reference pressure curves are stored, and the pressure curve evaluation means is formed in such a way that it carries out a comparison with the reference pressure curves during the evaluation.

4. Compressed air control device according to claim 2, wherein the flow control device is fed by an air supply means and by an oxygen supply means and is formed in such a way that it can adjust a concentration ratio of air and oxygen.

5. Compressed air control device according to claim 1, wherein the pressure curve evaluation means for recognising the start of natural breathing reflexes detects whether the pressure has a predetermined trailing edge.

6. Compressed air control device according to claim 1, wherein each pressure pulse is substantially rectangular.

7. CPAP system comprising a compressed air control device according to claim 1 and a CPAP device which comprises:
   a first opening, provided in a side wall of the hollow body, for supplying the modulated compressed air stream and for removing an exhaled air stream;
   a connecting piece which can be attached to the hollow body for connecting the hollow body to a nose attachment;
   a flow nozzle for directing the modulated air stream towards the first opening; and
   a second opening, provided in a side wall of the hollow body, for attaching the pressure detection device.

8. CPAP system according to claim 7, wherein the hollow body substantially has the shape of a hollow cylinder, to one end face of which the connecting piece can be attached and in the outer surface of which the opening is provided.

9. CPAP system according to claim 7, wherein the second opening is provided in a side wall of the hollow body other than the side wall having the first opening.

10. CPAP system according to claim 9, wherein the hollow body substantially has the shape of a hollow cylinder, to one end face of which the connecting piece can be attached, at the other end face of which the second opening is provided, and in the outer surface of which the first opening is provided.

11. CPAP system according to claim 10, wherein a pipe for connection to a pressure sensing line is connected to the second opening at substantially a right angle.

* * * * *